US00PP31204P3

(12) United States Plant Patent
Probasco et al.

(10) Patent No.: US PP31,204 P3
(45) Date of Patent: Dec. 10, 2019

(54) HOP PLANT NAMED 'HBC 638'

(50) Latin Name: *Humulus lupulus*
Varietal Denomination: HBC 638

(71) Applicant: HOP BREEDING COMPANY, L.L.C., Yakima, WA (US)

(72) Inventors: Eugene G. Probasco, Yakima, WA (US); Jason Perrault, Toppenish, WA (US)

(73) Assignee: Hop Breeding Company, L.L.C., Yakima, WA (US)

( * ) Notice: Subject to any disclaimer, the term of this patent is extended or adjusted under 35 U.S.C. 154(b) by 0 days.

(21) Appl. No.: 15/732,376

(22) Filed: Oct. 31, 2017

(65) Prior Publication Data

US 2018/0139878 P1 May 17, 2018

Related U.S. Application Data

(60) Provisional application No. 62/496,943, filed on Nov. 1, 2016.

(51) Int. Cl.
*A01H 5/02* (2018.01)
*A01H 6/28* (2018.01)

(52) U.S. Cl.
USPC ..... Plt./236
CPC ..... *A01H 5/02* (2013.01); *A01H 6/28* (2018.05)

(58) Field of Classification Search
USPC ..... Plt./236
See application file for complete search history.

*Primary Examiner* — Anne Marie Grunberg
(74) *Attorney, Agent, or Firm* — Svendsen Legal, LLC

(57) ABSTRACT

A new hop plant named 'HBC 638' is disclosed. 'HBC 638' is used for its exceptional and unique aromatic qualities, especially in the brewing of beer.

6 Drawing Sheets

Genus and species: *Humulus lupulus*.
Variety denomination: 'HBC 638'.

STATEMENT REGARDING FEDERALLY SPONSORED RESEARCH OR DEVELOPMENT

None

BACKGROUND OF THE INVENTION

'HBC 638' is a product of a controlled breeding program carried out by the inventors in the Yakima Valley of Washington State. 'HBC 638' was one of several seedlings resulting from a controlled cross made in 2008 with female parent 'HBC 366' (a patented variety under U.S. Plant Pat. No. 25,899), and male parent '21-10-21'. Seedling plants from this cross were planted in 2009 and screened for disease resistance and sex in a greenhouse and field nursery near Granger, Wash. A single plant of 'HBC 638' was selected in 2011. In 2012 'HBC 638' was asexually reproduced via softwood cuttings, and expanded to 14 plants in an evaluation block near Toppenish, Wash. In 2014 'HBC 638' was further expanded to a 1 acre test block near Toppenish, Wash. with plants asexually reproduced via softwood cuttings. The 'HBC 638' plants have now been observed and evaluated for several years. Throughout several generations of asexual propagation, 'HBC 638' has been observed to retain its distinctive characteristics and remain true to type.

COMPARISON OF 'HBC 638' TO PARENT PLANT AND COMARISON CULTIVAR

Table 1. below, sets forth some of the distinguishing characteristics of 'HBC 638' as compared to its female parent 'HBC 366', and to the 'Chinook' cultivar as a closely comparable cultivar.

TABLE 1

| | INSTANT CV. 'HBC 638' | FEMALE PARENT 'HBC 366' | COMPARISON CV. 'CHINOOK' |
|---|---|---|---|
| Alpha (% of cone weight) | 13.5-14.5 | 14-17 | 11.5-15 |
| Beta (% of cone weight) | 3.5-5.5 | 4.0-5.0 | 3.0-4.0 |
| Co-humulone (% of alpha acids) | 28.5-30.5 | 35-38 | 27-31 |
| Total Oil (mL/100 g) | 2.3-3.3 | 2.4-2.7 | 1.0-2.5 |
| Aromas | citrus (lemon-lime), tropical, lime, floral, pine, and cedar | apple, berry, mango, melon, and papaya | grapefruit, spice, and pine |

BRIEF DESCRIPTION OF THE PHOTOGRAPHS

Figure 1:
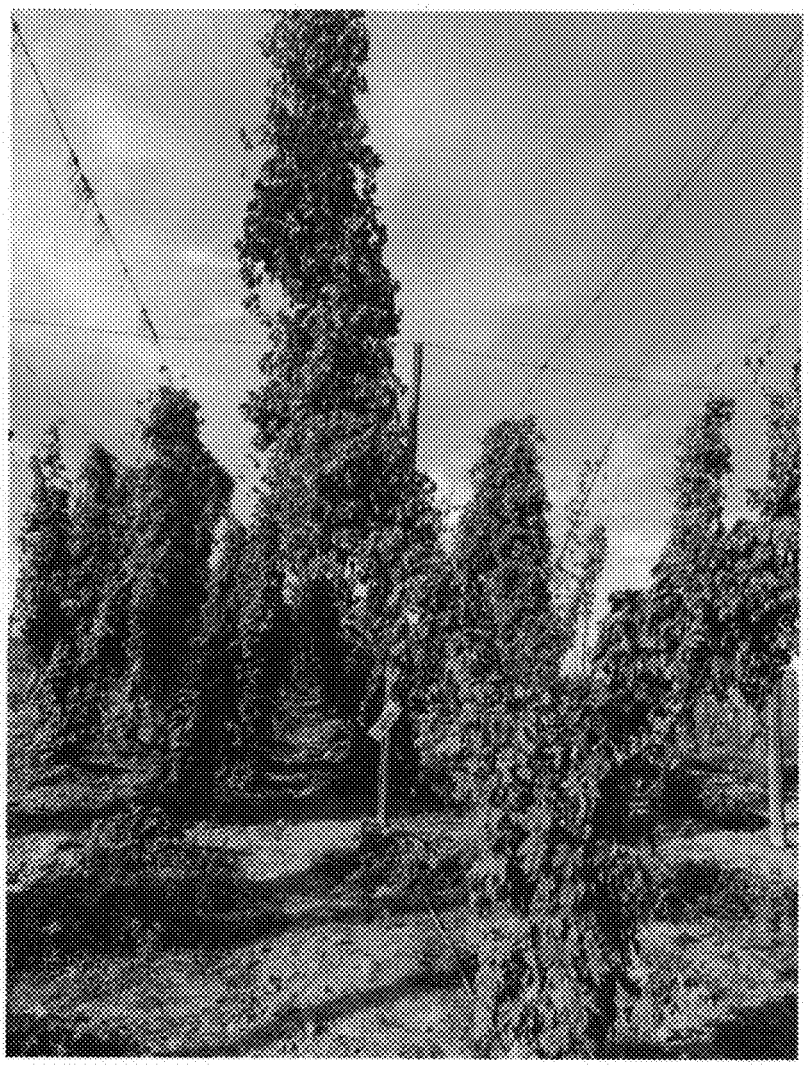
FIG. 1 illustrates a mature 'HBC 638' hop plant grown on a trellis.
Figure 2:
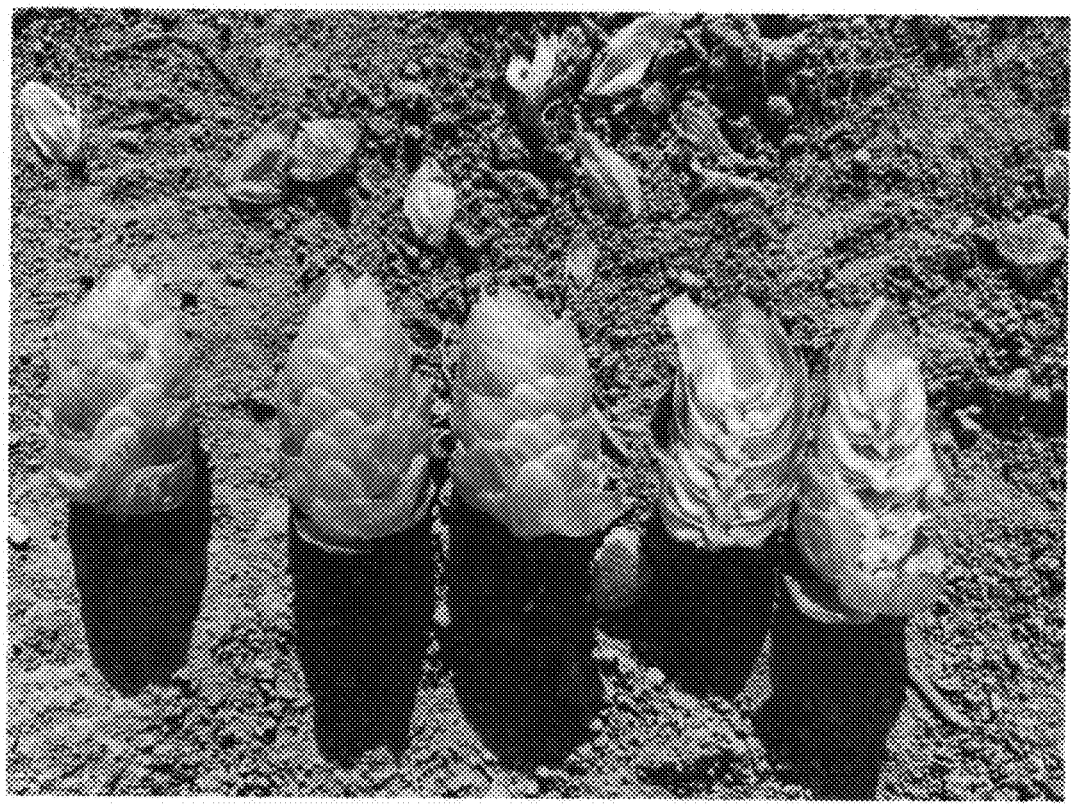
FIG. 2 illustrates whole cones and cross sections of cones of the 'HBC 638' hop plant.
Figure 3:
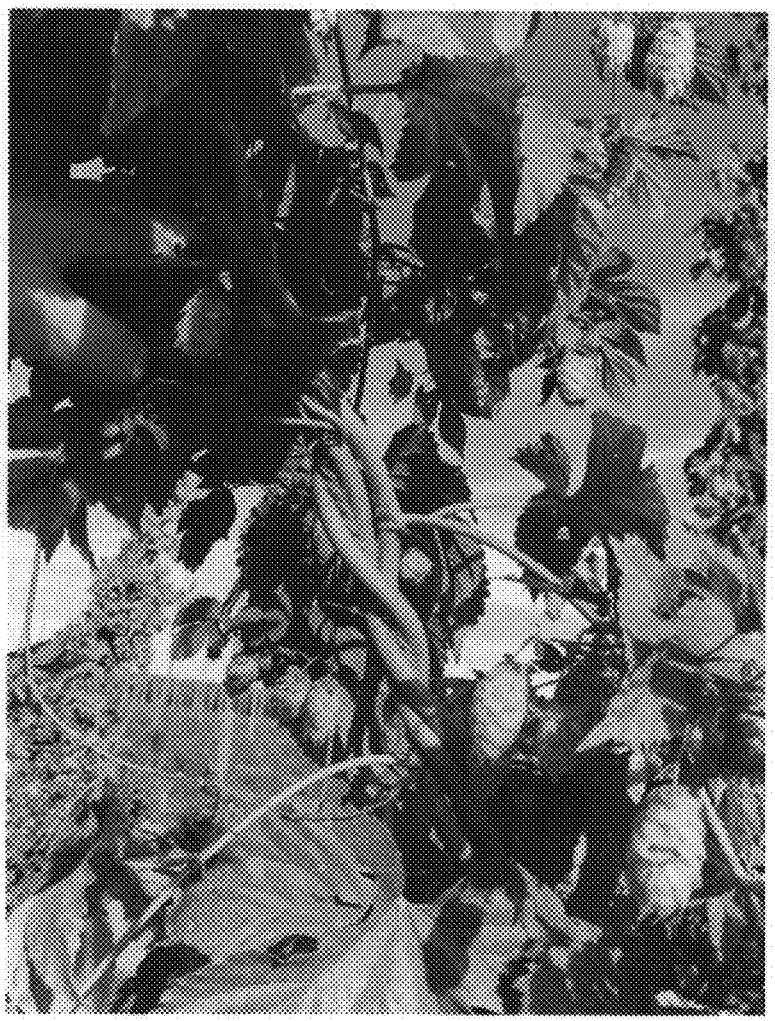
FIG. 3 illustrates the bine of a mature 'HBC 638' hop plant.
Figure 4:
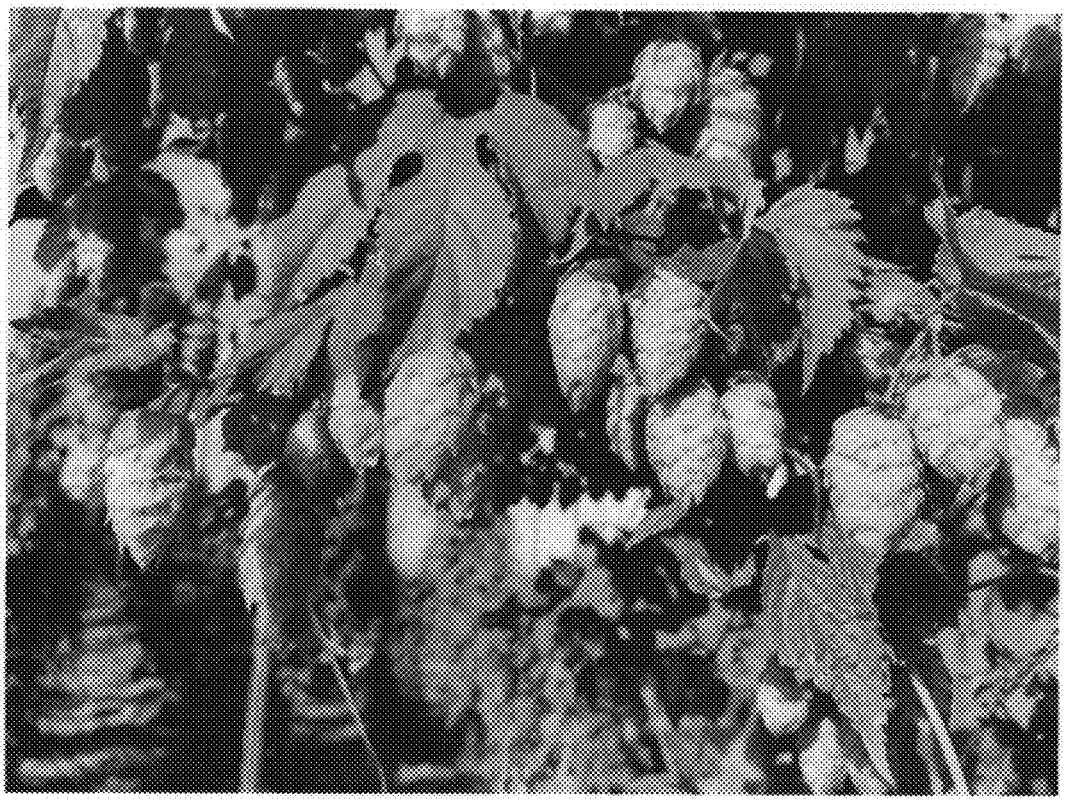
FIG. 4 illustrates cones on a mature 'HBC 638' hop plant.
Figure 5:
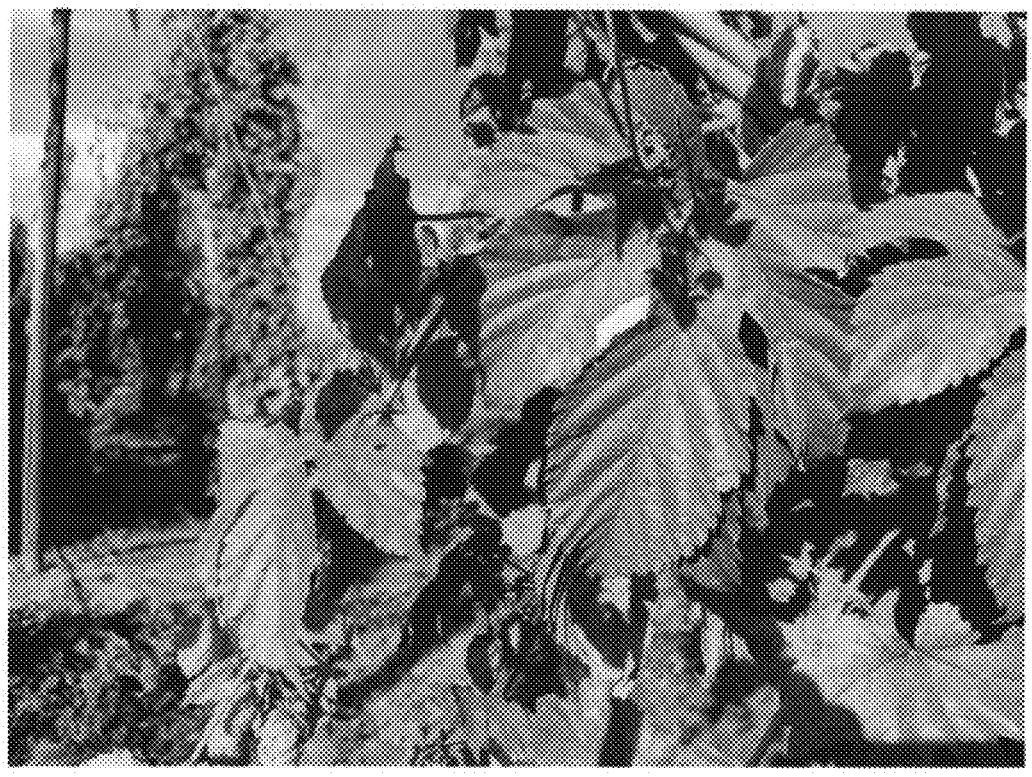
FIG. 5 illustrates leaves on a mature 'HBC 638' hop plant.
Figure 6:
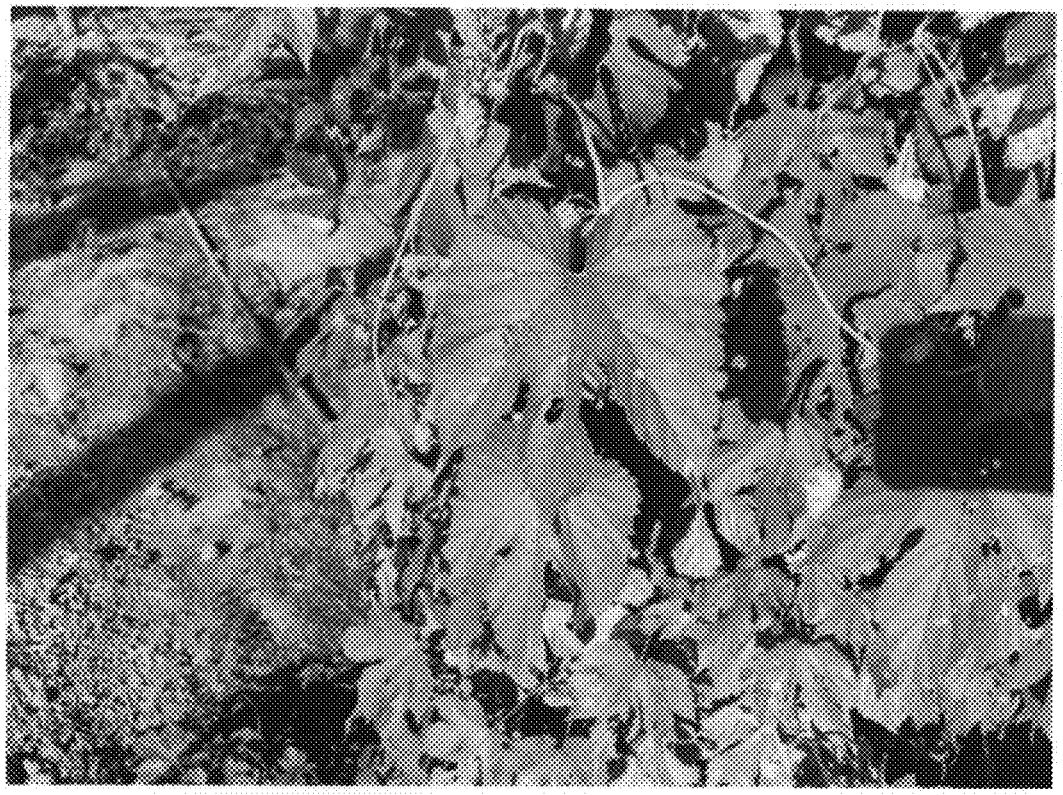
FIG. 6 illustrates an additional view of leaves on a mature 'HBC 638' hop plant.

The colors of these illustrations may vary with lighting conditions and, therefore, color characteristics of this new variety should be determined with reference to the observations described herein, rather than from these illustrations alone.

DETAILED BOTANICAL DESCRIPTION

The following description is based on observations made during the 2016 growing seasons at Toppenish, Wash. It should be understood that the characteristics described will vary somewhat depending upon cultural practices and climatic conditions, and can vary with location and season. Quantified measurements are expressed as an average of measurements taken from a number of individual plants of the new variety. The measurements of any individual plant or any group of plants, of the new variety may vary from the stated average. All color references are based on the 2001 edition of The Royal Horticultural Society Colour Chart.

Ploidy: Diploid (2n=2x).

Sex: Female.

Use: Brewing beer and ale.

Harvest date: September 20 to September 25 (during 2014 to 2016 growing seasons at Toppenish, Wash.).

Yield: Average yield is 2020 kg/hectare to 2450 kg/hectare.

Disease reaction:

*Powdery mildew.*—Resistant.

*Downy mildew.*—Unknown.

*Verticillium wilt.*—Unknown.

TABLE 2

| Oil Analytical Characteristics (Averages): | |
|---|---|
| % Alpha Acid (% cone weight) | 13.5 to 14.5% |
| % Beta Acid (% cone weight) | 3.5 to 5.5% |
| % Cohumulone (% alpha acids) | 28.5 to 30.5% |
| Total Oil (ml/100 g of cones): | 2.30 to 3.30% Oil |
| Hop Storage Index | <20% |
| Aroma Profile | Citrus (lemon-lime), tropical, floral, pine, cedar |
| A-Pinene: | 0.07% Total Oil |
| B-Pinene: | 0.48% Total Oil |
| Myrcene: | 37.58% Total Oil |
| 2-methyl-butyl isobutyrate: | 1.48% Total Oil |
| Limonene: | 0.16% Total Oil |
| Linalool: | 0.31% Total Oil |
| Caryophyllene: | 11.42% Total Oil |
| Farnesene: | 0.12% Total Oil |
| Humulene: | 17.76% Total Oil |
| Citral: | 1.27% Total Oil |
| Geranyl Acetate: | 0.06% Total Oil |
| Citronellol: | 3.60% Total Oil |
| Nerol: | 0.39% Total Oil |
| Geraniol: | 0.19% Total Oil |
| B-Ionene: | 0.01% Total Oil |

Plant growth type and shape: Climbing Bine, Normal (not dwarf), Cylindrical.

Bine:

*Color.*—Yellow-Green 145B.

*Stripe present.*—Yes.

*Stripe color.*—Red-Purple 60B.

*Stipule direction.*—Up.

*Typical and observed bine length.*—Typical bine growth of 18 feet to 25 feet, when grown on a standard eighteen foot trellis.

*Bine diameter.*—9.4 mm at base; 9.6 mm at nine feet; 7.8 mm at terminal end of eighteen feet.

Lateral:

*Lateral length in the middle third of plant.*—100 cm to 122 cm, on average.

*Lateral density in the middle third of plant.*—Two laterals per/node.

*Density of foliage in the middle third of plant.*—Medium.

*Lateral length in the upper third of plant.*—100 cm to 122 cm, on average.

*Lateral density in the upper third of plant.*—Two laterals per/node.

*Density of foliage in the upper third of plant.*—Medium.

Leaf:

*Arrangement.*—Opposite.

*Shape.*—Palmate.

*Average length of mature leaf.*—13.7 cm.

*Average width of mature leaf.*—15.3 cm.

*Color of mature leaf upper surface.*—Yellow-Green 147A.

*Color of mature leaf lower surface.*—Yellow-Green 147B.

*Color of immature leaf upper surface.*—Yellow-Green 146B.

*Color of immature leaf lower surface.*—Yellow-Green 147B.

*Number of lobes.*—1, 3, or 5.

*Margin.*—Serrate.

*Serrations per inch.*—5 to 7.

*Average petiole length (mature).*—81 mm.

*Petiole color at base.*—Yellow-Green 144B.

*Venation.*—Palmate.

*Vein color.*—Yellow-Green 144B.

Cone:

*Avg. length.*—31 mm.

*Avg. diameter.*—15 mm.

*Bract tip color.*—Yellow-Green 144A.

*Bract base color.*—Yellow-Green 145A.

*Bracteole color.*—Yellow-Green 145B.

*Cone shape.*—Ovate.

*Bract shape.*—Ovate.

*Bract tip shape.*—Acuminate-Mucronate.

*Bract tip position.*—Recurved.

*Degree of bract opening.*—Closed.

*Bract average length.*—14 mm to 17 mm.

*Bract average width.*—12 mm to 13 mm.

*Bracteole shape.*—Oval.

*Observed appearance of female inflorescences.*—Middle July to Late July.

*Pickability.*—Good.

*Average cone weight.*—788 mg.

*Lupulin glands color.*—Yellow 4A.

What is claimed:

1. A new and distinct Hop plant as illustrated and described herein.

* * * * *